United States Patent [19]

Willis et al.

[11] 4,382,972

[45] May 10, 1983

[54] FLAVORING COMPOSITIONS AND FLAVORED COMESTIBLES CONTAINING ALKYL 2,3-DIHYDRO-3(1'-HYDROXYALK-YLIDENE)-2-OXO-5-ALKYLFURAN-4-CARBOXYLATES

[75] Inventors: Brian J. Willis, Ramsey, N.J.; Frank Fischetti, Jr., Flushing; Robert G. Eilerman, Merrick, both of N.Y.

[73] Assignee: Fritzsche Dodge & Olcott Inc., New York, N.Y.

[21] Appl. No.: 264,806

[22] Filed: May 18, 1981

Related U.S. Application Data

[60] Continuation-in-part of Ser. No. 72,281, Sep. 4, 1979, abandoned, which is a continuation-in-part of Ser. No. 908,267, May 27, 1978, abandoned, which is a division of Ser. No. 698,742, Aug. 4, 1975, Pat. No. 4,109,662, which is a continuation-in-part of Ser. No. 601,482, Aug. 4, 1975, abandoned.

[51] Int. Cl.$^3$ ............... A23L 1/226; A23L 1/235
[52] U.S. Cl. ............... 426/536; 549/322
[58] Field of Search ............... 426/536; 260/343.6; 549/322

[56] References Cited

U.S. PATENT DOCUMENTS 4,109,662   8/1978   Willis et al. ............... 426/538 X

*Primary Examiner*—Joseph M. Golian
*Attorney, Agent, or Firm*—Cooper, Dunham, Clark, Griffin & Moran

[57] ABSTRACT

The flavoring compositions and flavored comestibles of this invention include alkyl 2,3-dihydro-3(1'-hydroxyalkylidene)-2-oxo-5-alkylfuran-4-carboxylates in amounts capable of significantly enhancing the flavor of the flavoring compositions or flavored comestibles. For example, butterscotch flavors are materially improved in smoothness and certain fruit flavors are given greater richness and ripeness when the carboxylates of this invention are incorporated therein. Similarly, fruit flavored carbonated soft drinks which include the carboxylates possess enhanced flavors.

13 Claims, No Drawings

FLAVORING COMPOSITIONS AND FLAVORED COMESTIBLES CONTAINING ALKYL 2,3-DIHYDRO-3(1′-HYDROXYALKYLIDENE)-2-OXO-5-ALKYLFURAN-4-CARBOXYLATES

This application is a continuation-in-part of U.S. Ser. No. 72,281, filed Sept. 4, 1979, now abandoned, which is a continuation-in-part of U.S. Ser. No. 908,267, filed May 22, 1978, now abandoned, which is a divisional of U.S. Ser. No. 698,742, filed Aug. 4, 1975, now U.S. Pat. No. 4,109,662, which is a continuation-in-part of U.S. Ser. No. 601,482, filed Aug. 4, 1975, now abandoned.

This invention relates generally to flavoring compositions and flavored comestibles and more particularly to flavoring compositions and flavored comestibles containing an alkyl 2,3-dihydro-3(1′-hydroxyalkylidene)-2-oxo-5-alkylfuran-4-carboxylate.

It is well known that synthetic flavor enhancers such as Maltol, Ethyl Maltol, and 4-hydroxy-2,5-dimethyl-3(2H)-furanone are useful as flavor enhancers. However, such flavor enhancers are very expensive and increase the cost of products in which they are used.

In accordance with this invention, certain alkyl 2,3-dihydro-3(1′-hydroxyalkylidene)-2-oxo-5-alkylfuran-4-carboxylates are added to a wide variety of flavoring compositions and flavored comestibles to impart significantly enhanced flavors. For example, butterscotch flavors are materially improved in smoothness. Strawberry flavors are given a striking freshness. Banana flavors are rounded out to give the flavor of a ripe banana. When added to smoking tobacco or synthetic tobacco, the resulting product is increased in sweetness, the taste of the smoke is softened and the flow of saliva is increased, which lessens dryness of the mouth during smoking. When added to cough syrup containing theophylline, the flavor enhancer of this invention covers up the bitter taste. This flavor enhancer can also be used to replace part of the sugar content of a wide variety of sweetened beverages and foods, producing excellent flavor at lower cost.

Alkyl, 2,3-dihydro-3(1′-hydroxyalkylidene)-2-oxo-5-alkylfuran-4-carboxylates employed in the flavoring compositions or flavored comestibles of this invention have the formula:

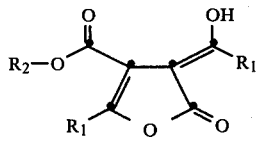

in which $R_1$ and $R_2$ are methyl or ethyl and may be the same or different, said carboxylate enhancing the flavor of said flavoring composition or flavored comestible.

The alkyl 2,3-dihydro-3(1′-hydroxyalkylidene)-2-oxo-5-alkylfuran-4-carboxylates may be prepared by the general methods of Knorr, Ber. 1889, 22, 158.

For example, the flavor enhancer, ethyl 2,3-dihydro-3(1′-hydroxyethylidene)-2-oxo-5-methylfuran-4-carboxylate is prepared as follows:

The starting material, diethyl $\alpha$, $\beta$-diacetylsuccinate, is produced by adding ethyl acetoacetate (130 g, 1 mol) dropwise in a nitrogen atmosphere to a suspension of sodium hydride (1.05 mol) in 600 ml of anhydrous ether. After one hour, a solution of iodine (127 g, 0.5 mol) in 600 ml of ether is added and the resulting mixture is stirred at ambient temperature for an additional one hour. The mixture is diluted with 500 ml of water. The ether phase is separated and washed with two 100 ml portions of aqueous sodium bisulfate and then dried over sodium sulfate. The filtered solution is stripped of solvent yielding 120 g (92%) of diethyl $\alpha\beta$-diacetyl-succinate. Recrystallization from 50% aqueous acetic acid gives 72 g of a solid form of the dimer, mp 89°–90° C.; IR (CHCl$_3$) 1775, 1730 cm$^{-1}$, NMR (CDCl$_3$), $\delta$1.25 (t,6H), 2.40 (s,6H), 4.18 (q,4H), 4.4 (s,2H).

Ethyl 2,3-dihydro-3(1′-hydroxyethylidene)-2-oxo-5-methylfuran-4-carboxylate is obtained by suspending under nitrogen diethyl $\alpha,\beta$-diacetylsuccinate (85 g, 0.33 mol) in 400 ml of anhydrous ethyl alcohol. Solid potassium hydroxide (0.35 mol) is added in one portion and the solution is brought to reflux over 30 minutes. Refluxing is continued for one hour and then the reaction mixture is cooled in an ice-water bath (10° C.). The solution is acidified by dropwise addition of 3N hydrochloric acid (120 ml). Water (50 ml) is added and cooling continued for one hour to ensure complete crystallization. The solid is isolated by filtration and washed with ice water until the washings are neutral. This yields 36 g (51%) of pure ethyl 2,3-dihydro-3(1′-hydroxyethylidene)-2-oxo-5-methylfuran-4-carboxylate, mp 106°–107.5° C., IR (CHCl$_3$), 1765, 1650, 1630 cm$^{-1}$, NMR (CDCl$_3$), $\delta$1.42 (t,3H), 2.45 (s,3H), 2.5 (s,3H), 4.4 (q,2H), 13.6(s,1H).

If the flavor enhancer desired is ethyl 2,3-dihydro-3(1′-hydroxypropylidene)-2-oxo-5-ethylfuran-4-carboxylate, the starting material is diethyl $\alpha,\beta$-dipropionylsuccinate, prepared as follows:

Ethyl 3-oxopentanoate (72 g, 0.5 mol) is added dropwise in a nitrogen atmosphere to a suspension of sodium hydride (0.52 mol) in 300 ml of 1:1 anhydrous ether-tetrahydrofuran. After one hour, a solution of iodine (63.5 g, 0.25 mol) in tetrahydrofuran (150 ml) is added and the resulting mixture stirred at ambient temperature for an additional one hour. Water (250 ml) is added and the phases separated. The ether solution is washed with two 50 ml portions of sodium sulfite and dried over sodium sulfate. Removal of the solvent affords 66 g (91%) of diethyl $\alpha,\beta$-dipropionylsuccinate. Recrystallization from hexane gives 29 g of solid dimer, mp 80–83 C; IR (CHCl$_3$) 1755, 1730 cm$^{-1}$; NMR (CDCl$_3$) 1.1 (t,6H), 1.3 (t,6H), 2.83 (d of q,4H), 4.18 (q,4H), 4.5 (s,2H).

Ethyl 2,3-dihydro-3(1′-hydroxypropylidene)-2-oxo-5-ethylfuran-4-carboxylate is obtained by combining 28 g of diethyl $\alpha,\beta$-dipropionylsuccinate (0.1 mol) and potassium hydroxide (0.11 mol) in 200 ml of absolute ethanol and bringing the mixture to reflux.

After one hour the mixture is cooled and poured into 450 ml of water. The aqueous mixture is extracted with benzene (2×150 ml) and the extracts discarded. The aqueous mixture is then acidified with 3N hydrochloric acid (60 ml) and extracted with benzene (3×100 ml). The organic layers are washed with brine and dried over sodium sulfate. Solvent removal gives 12.6 g of crude material. Short path distillation affords 9.5 g of pure product bp 150°–154° C./0.5 mm; IR (neat) 1760, 1645, 1615 cm$^{-1}$; NMR (CDCl$_3$) 1.15 (t,3H), 1.22 (t,3H), 1.41 (t,3H), 2.85 (q,2H), 2.92 (q,2H), 4.45 (q,2H), 13.5 (s,1H).

The flavored comestibles of this invention comprise at least 0.0001% by weight of one or more alkyl 2,3-dihydro-3(1′-hydroxyalkylidene)-2-oxo-5-alkylfuran-4-carboxylate. The amount of alkyl 2,3-dihydro-3(1′-hydroxyalkylidene)-2-oxo-5-alkylfuran-4-carboxylate may vary within a wide range such as about 0.0001% to 1.0% by weight. More advantageously the range may be between about 0.001% and 0.5% by weight of the flavored comestible composition and preferably between about 0.0025% and 0.1% by weight.

The flavoring compositions of this invention comprise at least 0.01% by weight of one or more alkyl 2,3-dihydro-3(1'-hydroxyalkylidene)-2-oxo-5-alkylfuran-4-carboxylate. The amount of alkyl 2,3-dihydro-3(1'-hydroxyalkylidene)-2-oxo-5-alkylfuran-4-carboxylate may vary within a wide range such as about 0.01% to 30% by weight. More advantageously, the range may be between about 0.1% and 20% by weight of the flavoring composition and preferably between about 0.5% and 10% by weight.

Examples of flavoring compositions in which the carboxylates may desirably be included are pineapple, butterscotch, banana, and strawberry flavoring compositions. Examples of flavored comestibles are foodstuffs, such as meats, protein sources, fruits, and cereals; soft drinks, wines; alcohol drinks; carbonated beverages; and a wide range of edible and drinkable sugar-containing compositions. The carboxylates may desirably also be included in smoking tobacco and in liquid medicaments, such as cough syrups.

Thus, the carboxylates of this invention may advantageously be incorporated into a wide range of flavoring compositions and flavored comestibles provided only that the carboxylates be capable of enhancing their flavors and be present in suitable amounts to effect flavor enhancement.

A more comprehensive understanding of this invention is obtained from the following examples. Examples I and II show compositions produced with two levels of concentration of ethyl 2,3-dihydro-3(1'-hydroxyethylidene)-2-oxo-5-methylfuran-4-carboxylate.

EXAMPLE I

| PINEAPPLE FLAVORING COMPOSITION | Parts by Weight | Parts by Weight |
|---|---|---|
| Allyl Cyclohexane Propionate | 1.4 | 1.4 |
| Geranyl Propionate | 0.5 | 0.5 |
| Allyl Caproate | 13.0 | 13.0 |
| Ethyl Iso Valerate | 1.0 | 1.0 |
| Ethyl Butyrate | 1.0 | 1.0 |
| Vanillin | 0.5 | 0.5 |
| Oil Orange | 1.0 | 1.0 |
| Maltol | 2.0 | 2.0 |
| Ethyl 2,3-Dihydro-3(1'-Hydroxyethylidene)-2-Oxo-5-Methylfuran-4-Carboxylate | 20.0 | 2.5 |
| Ethyl Alcohol 95% | 46.0 | 46.0 |
| Propylene Glycol | 13.6 | 31.1 |
| | 100.0 | 100.0 |

EXAMPLE II

| STRAWBERRY FLAVORING COMPOSITION | Parts by Weight | Parts by Weight |
|---|---|---|
| Methoxy Phenyl Butanone | 1.0 | 1.0 |
| Ethyl Butyrate | 6.0 | 6.0 |
| Ethyl Iso Valerate | 2.0 | 2.0 |
| Benzyl Butyrate | 1.5 | 1.5 |
| Benzyl Iso Valerate | 0.5 | 0.5 |
| cis-3-Hexenol | 3.0 | 3.0 |
| Isobutyric Acid | 1.5 | 1.5 |

-continued

| STRAWBERRY FLAVORING COMPOSITION | Parts by Weight | Parts by Weight |
|---|---|---|
| Diacetyl | 0.2 | 0.2 |
| Butyl Phenylacetate | 0.4 | 0.4 |
| Acetaldehyde 50% in Ethanol | 0.2 | 0.2 |
| Benzyl Dipropyl Ketone | 0.2 | 0.2 |
| 2-Heptanone | 0.1 | 0.1 |
| Ethyl Methyl Phenyl Glycidate | 2.4 | 2.4 |
| Ethyl 2,3-Dihydro-3(1'-Hydroxyethylidene)-2-Oxo-5-Methylfuran-4-Carboxylate | 30.0 | 5.0 |
| Propylene Glycol | 51.0 | 51.0 |
| Benzyl Alcohol | — | 25.0 |
| | 100.0 | 100.0 |

EXAMPLE III

| BUTTERSCOTCH FLAVORING COMPOSITION | Parts by Weight |
|---|---|
| Ethyl 2,3-dihydro-3(1'-Hydroxyethylidene)-2-Oxo-5-Methylfuran-4-Carboxylate | 1.0 |
| Butyl Butyrolactate | 4.0 |
| Diacetyl | 0.2 |
| Ethyl Oleate | 2.0 |
| Ethyl Myristate | 0.5 |
| Vanillin | 0.5 |
| Acetoin | 0.3 |
| Phenylethanol | 0.2 |
| Butyric Acid | 0.1 |
| Ethyl Oxyhydrate | 0.1 |
| Ethyl Maltol | 3.0 |
| Δ-Decalactone | 0.3 |
| γ-Nonalactone | 0.1 |
| Tincture Foenugreek | 0.4 |
| Methyl Cyclopentene-ol-one | 0.1 |
| Benzyl Alcohol | 26.0 |
| Propylene Glycol | 60.2 |
| | 100.0 |

EXAMPLE IV

| BANANA FLAVORING COMPOSITION | Parts by Weight |
|---|---|
| Iso Amyl Acetate | 12.0 |
| Iso Amyl Butyrate | 10.0 |
| Benzyl Butyrate | 3.0 |
| Iso Amyl Iso Valerate | 2.0 |
| Ethyl butyrate | 3.0 |
| Butyric Acid | 1.5 |
| Oil Lemon | 2.5 |
| Vanillin | 2.5 |
| Ethyl Maltol | 0.5 |
| γ-Undecalactone | 0.4 |
| 4-(p-Hydroxyphenyl)-2-Butanone | 0.1 |
| Ethyl 2,3-Dihydro-3(1'-Hydroxyethylidene)-2-Oxo-5-Methylfuran-4-Carboxylate | 10.0 |
| Propylene Glycol | 52.5 |
| | 100.0 |

EXAMPLE V

| BUTTERSCOTCH FLAVORING COMPOSITION | VA | VB |
|---|---|---|
| Butyl Butyrolactate | 4.0 | 4.0 |
| Diacetyl | 0.2 | 0.2 |
| Ethyl Oleate | 2.0 | 2.0 |

| BUTTERSCOTCH FLAVORING COMPOSITION | | |
|---|---|---|
| | VA | VB |
| Ethyl Myristate | 0.5 | 0.5 |
| Vanillin | 1.5 | 1.5 |
| Acetyl Methyl Carbinol | 0.3 | 0.3 |
| Phenyl Ethyl Alcohol | 0.2 | 0.2 |
| Butyric Acid | 0.1 | 0.1 |
| Ethyl Oxyhydrate | 0.1 | 0.1 |
| Ethyl Maltol | 3.0 | — |
| Ethyl 2,3-Dihydro-3(1'-Hydroxyethylidene)-2-Oxo-5-Methylfuran-4-Carboxylate | 1.0 | 5.0 |
| Δ-Decalactone | 0.3 | 0.3 |
| γ-Nonalactone | 0.1 | 0.1 |
| Tincture Foenugreek | 0.4 | 0.4 |
| Methyl Cyclopenten-ol-one | 0.1 | 0.1 |
| Benzyl Alcohol | 26.0 | 26.0 |
| Propylene Glycol | 60.2 | 59.2 |
| | 100.0 | 100.0 |

Formula VA contains Ethyl Maltol in addition to ethyl 2,3-dihydro-3(1'-hydroxyethylidene)-2-oxo-5-methylfuran-4-carboxylate, while Formula VB contains only the carboxylate as a complete replacement for Ethyl Maltol. The butterscotch flavor achieved by Formula VB is richer and smoother.

The replacement proportion of Ethyl Maltol by ethyl 2,3-dihydro-3(1'-hydroxyethylidene)-2-oxo-5-methylfuran-4-carboxylate is approximately one and one-half parts by weight of the carboxylate for one part by weight of Ethyl Maltol.

EXAMPLE VI

WINE FLAVORING COMPOSITION AND WINE CONTAINING SAME

A wine flavoring composition is produced by adding 0.08 parts by weight of ethyl 2,3-dihydro-3(1'hydroxyethylidene)-2-oxo-5-methylfuran-4-carboxylate to 99.92 parts by weight of a natural wine flavor. Four liquid ounces of the resulting wine concentrate are added to one gallon of wine to produce a wine having enhanced flavor character.

A wine flavoring composition may also be produced by preparing a 1% by weight ethanol solution of ethyl 2,3-dihydro-3(1'-hydroxyethylidene)-2-oxo-5-methylfuran-4-carboxylate and adding 0.32 fluid ounces of the solution to 1 gallon of wine. This is equivalent to 25 parts per million. The resulting wine possesses enhanced flavor character.

EXAMPLE VII

FLAVORED TOBACCO COMPOSITION

A 1% ethanol solution of ethyl 2,3-dihydro-3(1'-hydroxy-ethylidene)-2-oxo-5-methylfuran-4-carboxylate is sprayed on flavored smoking tobacco at the rate of 4 ounces of solution per 100 pounds of tobacco. After the alcohol is allowed to evaporate, a flavored tobacco composition results which has enhanced flavor character.

To produce a flavored tobacco product which also contains synthetic tobacco, the procedure for production of flavored tobacco composition heretofore described in this example is repeated except that instead of employing smoking tobacco only, synthetic tobacco such as cellulose fibers, for example, the cellulose fibers sold by the Celanese Chemical Company under the trademark "CYTREL" or the cellulose fibers sold by Imperial Chemical Corporation under the trademark "Polystrep", is blended with the flavored tobacco in a ratio of approximately 1 to 1 by weight.

In a third procedure, a 1% ethanol solution of ethyl 2,3-dihydro-3(1'-hydroxyethylidene)-2-oxo-5-methylfuran-4-carboxylate is sprayed on synthetic tobacco, such as cellulose fibers, at the rate of 4 ounces of solution to 100 pounds of synthetic tobacco. After the alcohol is allowed to evaporate, a flavored tobacco synthetic composition results.

Any one of the above flavored tobacco compositions may be used in cigarettes, producing a striking improvement in flavor.

EXAMPLE VIII

CARBONATED SOFT DRINKS

A fruit flavored carbonated soft drink is produced by dissolving one ounce by weight of one of the flavoring compositions such as described in Examples I or II in one gallon of sugar syrup. One ounce of the resulting mixture is added to about five ounces of carbonated water to produce six ounces of a carbonated beverage having enhanced flavor.

The flavoring composition of Example I containing 2.5% by weight of ethyl 2,3-dihydro-3(1'-hydroxyethylidene)-2-oxo-5-methylfuran-4-carboxylate results in a level of 32 parts per million of ethyl 2,3-dihydro-3(1'-hydroxy-ethylidene)-2-oxo-5-methylfuran-4-carboxylate flavor enhancer in the total carbonated drink produced.

EXAMPLE IX

BUTTERSCOTCH FLAVORING COMPOSITION

A butterscotch composition containing a flavor enhancer in accordance with the teaching of the invention was prepared. For comparison, another composition containing the same ingredients but without the flavor enhancer was also prepared as a control. The formulae of the compositions are as follows:

| | Parts by Weight (Control) | Parts by Weight |
|---|---|---|
| Butyl butyrolactate | 4.0 | 4.0 |
| Diacetyl | 0.2 | 0.2 |
| Ethyl Oleate | 2.0 | 2.0 |
| Ethyl Myristate | 0.5 | 0.5 |
| Vanillin | 1.5 | 1.5 |
| Acetyl Methyl Carbinol | 0.3 | 0.3 |
| Phenyl Ethyl Alcohol | 0.2 | 0.2 |
| Butyric Acid | 0.1 | 0.1 |
| Ethyl Propionate | 0.1 | 0.1 |
| Ethyl Maltol | 3.0 | 3.0 |
| Δ-Decalactone | 0.3 | 0.3 |
| γ-Nonalactone | 0.1 | 0.1 |
| Methyl Para-Tertiary Butyl Phenylacetate (1% in alcohol) | 0.1 | 0.1 |
| Tincture Foenugreek | 0.4 | 0.4 |
| Cyclotene | 0.1 | 0.1 |
| Benzyl Alcohol | 27.1 | 27.1 |
| Propylene Glycol | 60.0 | 57.0 |
| Ethyl 2,3-Dihydro-3(1'-Hydroxypropylidene)-2-Oxo-5-Ethylfuran-4-Carboxylate | — | 3.0 |
| | 100.0 | 100.0 |

The butterscotch composition containing the flavor enhancer has an immeasurably superior flavor over the control.

The particular alkyl 2,3-dihydro-3(1'-hydroxyalkylidene)-2-oxo-5-alkylfuran-4-carboxylate specified in each of the Examples I–IX may be replaced in any of those examples with an equal quantity of any of the compounds falling within the scope of the claims of the invention.

For instance, in Example IV, 10 parts by weight of methyl 2,3-dihydro-3(1'-hydroxyethylidene)-2-oxo-5-methylfuran-4-carboxylate may be substituted for 10 parts by weight of ethyl 2,3-dihydro-3(1'-hydroxyethylidene)-2-oxo-5-methylfuran-4-carboxylate included in the formulation in Example IV.

What is claimed is:

1. A flavoring composition having enhanced flavor character comprising an alkyl 2,3-dihydro-3(1'-hydroxyalkylidene)-2-oxo-5-alkylfuran-4-carboxylate having the structure:

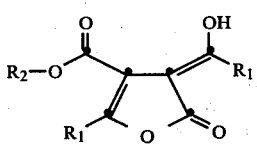

wherein each of $R_1$ and $R_2$ is methyl or ethyl and is the same or different and conventional flavoring ingredients, said carboxylate being present in an amount 0.01% to 30% by weight which is effective in enhancing the flavor of said flavoring ingredients, said flavoring ingredients comprising pineapple, butterscotch, banana and strawberry flavoring compositions.

2. A flavoring composition in accordance with claim 1 wherein said amount is an amount from about 0.1% to 20% by weight.

3. A flavoring composition in accordance with claim 1 wherein said amount is an amount from about 0.5% to 10.0% by weight.

4. A flavoring composition in accordance with claim 1 in which the alkyl 2,3-dihydro-3(1'-hydroxyalkylidene)-2-oxo-5-alkylfuran-4-carboxylate is ethyl 2,3-dihydro-3(1'-hydroxyethylidene)-2-oxo-5-methylfuran-4-carboxylate.

5. A flavoring composition in accordance with claim 1 in which the alkyl 2,3-dihydro-3(1'-hydroxyalkylidene)-2-oxo-5-alkylfuran-4-carboxylate is ethyl 2,3-dihydro-3(1'-hydroxypropylidene)-2-oxo-5-ethylfuran-4-carboxylate.

6. A flavoring composition in accordance with claim 1 in which the alkyl 2,3-dihydro-3(1'-hydroxyalkylidene)-2-oxo-5-alkylfuran-4-carboxylate is methyl 2,3-dihydro-3(1'-hydroxyethylidene)-2-oxo-5-methylfuran-4-carboxylate.

7. A flavored comestible having enhanced flavor character comprising an alkyl 2,3-dihydro-3(1'-hydroxyalkylidene)-2-oxo-5-akylfuran-4-carboxylate having the structure:

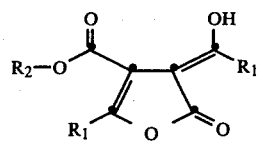

wherein each of $R_1$ and $R_2$ is methyl or ethyl and is the same or different and conventional flavored comestible ingredients selected from the group consisting of foodstuffs, soft drinks and alcoholic beverages, said carboxylate being present in an amount 0.0001% to 1.0% by weight which is effective in enhancing the flavor of said flavored comestible ingredients.

8. A flavored comestible in accordance with claim 7 wherein said amount is an amount from about 0.001% to 0.5% by weight.

9. A flavored comestible in accordance with claim 7 wherein said amount is an amount from about 0.0025% to 0.1% by weight.

10. A flavored comestible in accordance with claim 7 in which the alkyl 2,3-dihydro-3(1'-hydroxyalkylidene)-2-oxo-5-alkylfuran-4-carboxylate is ethyl 2,3-dihydro-3(1'-hydroxyethylidene)-2-oxo-5-methylfuran-4-carboxylate.

11. A flavored comestible in accordance with claim 7 in which the alkyl 2,3-dihydro-3(1'-hydroxyalkylidene)-2-oxo-5-alkylfuran-4-carboxylate is ethyl 2,3-dihydro-3(1'-hydroxypropylidene)-2-oxo-5-ethylfuran-4-carboxylate.

12. A flavored comestible in accordance with claim 7 in which the alkyl 2,3-dihydro-3(1'-hydroxyalkylidene)-2-oxo-5-alkylfuran-4-carboxylate is methyl 2,3-dihydro-3(1'-hydroxyethylidene)-2-oxo-5-methylfuran-4-carboxylate.

13. A method of enhancing the flavor of a flavored comestible selected from the group consisting of foodstuffs, soft drinks and alcoholic beverages which comprises adding to or incorporating in said flavored comestible an effective flavor enhancing amount of 0.0001% to 1.0% by weight of an alkyl 2,3-dihydro-3(1'-hydroxy-alkylidene)-2-oxo-5-alkylfuran-4-carboxylate having the structure:

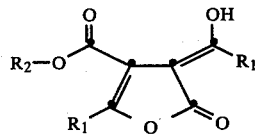

wherein each of $R_1$ and $R_2$ is methyl or ethyl and is the same or different.

* * * * *